United States Patent
Piech et al.

(10) Patent No.: US 7,705,336 B2
(45) Date of Patent: Apr. 27, 2010

(54) OPTICAL INTERROGATION SYSTEM AND METHOD FOR INCREASING A READ-OUT SPEED OF A SPECTROMETER

(75) Inventors: Garrett A. Piech, Horseheads, NY (US); Michael B. Webb, Lindley, NY (US)

(73) Assignee: Corning Incorporated, Corning, NY (US)

( * ) Notice: Subject to any disclaimer, the term of this patent is extended or adjusted under 35 U.S.C. 154(b) by 839 days.

(21) Appl. No.: 11/500,048

(22) Filed: Aug. 7, 2006

(65) Prior Publication Data
US 2007/0031291 A1 Feb. 8, 2007

Related U.S. Application Data

(60) Provisional application No. 60/706,832, filed on Aug. 8, 2005.

(51) Int. Cl.
*G01N 21/00* (2006.01)
(52) U.S. Cl. .............. 250/559.05; 250/559.4; 250/216
(58) Field of Classification Search .......... 250/208.1, 250/559.01–559.43, 226
See application file for complete search history.

(56) References Cited

U.S. PATENT DOCUMENTS

| | | | |
|---|---|---|---|
| 4,674,880 A | 6/1987 | Seki | 356/328 |
| 4,815,843 A | 3/1989 | Tiefenthaler et al. | 356/128 |
| 5,355,165 A | 10/1994 | Kosonocky et al. | 348/311 |
| 5,675,411 A | 10/1997 | Brooks et al. | 356/328 |
| 6,255,134 B1 | 7/2001 | Hori | 438/75 |
| 6,633,331 B1 | 10/2003 | Potter et al. | 348/207.11 |
| 6,638,787 B1 * | 10/2003 | Buchin et al. | 438/75 |
| 6,785,433 B2 | 8/2004 | Tiefenthaler | 385/12 |
| 6,829,073 B1 | 12/2004 | Krol et al. | 359/263 |
| 7,057,720 B2 | 6/2006 | Caracci et al. | 356/300 |
| 2001/0040130 A1 * | 11/2001 | Lorch et al. | 210/601 |
| 2003/0077660 A1 * | 4/2003 | Pien et al. | 435/7.1 |
| 2005/0099622 A1 | 5/2005 | Caracci et al. | 356/300 |
| 2005/0236554 A1 | 10/2005 | Fontaine et al. | 250/208.1 |

(Continued)

OTHER PUBLICATIONS

U.S. Appl. No. 11/058,155, filed Feb. 14, 2005, J. Gollier et al.

(Continued)

*Primary Examiner*—Georgia Y Epps
*Assistant Examiner*—Tony Ko
(74) *Attorney, Agent, or Firm*—Timothy M Schaeberle; Thomas R Beall; William J Tucker

(57) ABSTRACT

A typical use of linear or two dimensional spectrometers is to expose the detector area, and then shift the photo-electric charges out of the device in a serial fashion. If the illuminating signal is spatially narrow relative to the size of the array, this will drive down the percent of the detector that is utilized, as only a relatively small number of pixels are used to detect the beam. The present invention proposes a method which capitalizes on this spatial under-utilization, and alters the clocking scheme to maximize the read-out speed of the pixels containing signal information. This type of clocking scheme raises the optical power saturation level of the spectrometer. Such an improvement in optical power handling is beneficial for spectrometer based detection of resonant waveguide grating biochemical binding, since in such systems the performance is frequently limited by spectrometer saturation.

10 Claims, 4 Drawing Sheets

U.S. PATENT DOCUMENTS

| | | | |
|---|---|---|---|
| 2005/0264818 A1 | 12/2005 | Gollier | 356/445 |
| 2005/0272046 A1* | 12/2005 | Schermer et al. | 435/6 |
| 2006/0024013 A1* | 2/2006 | Magnusson et al. | 385/129 |
| 2006/0093254 A1 | 5/2006 | Mozdy | 385/12 |
| 2006/0141611 A1 | 6/2006 | Frutos et al. | 435/287.2 |

OTHER PUBLICATIONS

U.S. Appl. No. 60/701,445, filed Jul. 20, 2005, S.J. Caracci et al.

S.P. Monacos et al., "A High Frame Rate CCD Camera with Region-of-Interest Capability", 2001 IEEE Aerospace Conference, Big Sky, Montana, pp. 1-10.

K. Tiefenthaler et al., "Integrated Optical Switches and Gas Sensors", Optics Letters, Apr. 1984, vol. 10, No. 4, pp. 137-139.

K. Tiefenthaler et al., "Sensitivity of Grating Couplers as Integrated-Optical Chemical Sensors", J. Opt. Soc. Am. B, Feb. 1989, vol. 6, No. 2, pp. 209-220.

W. Lukosz, "Integrated Optical Chemical and Direct Biochemical Sensors", Sensors and Actuators B, vol. 29, 1995, pp. 37-50.

* cited by examiner

OPTICAL INTERROGATION SYSTEM AND METHOD FOR INCREASING A READ-OUT SPEED OF A SPECTROMETER

CLAIMING BENEFIT OF PROVISIONAL APPLICATION

This application claims the benefit of U.S. Provisional Application Ser. No. 60/706,832 filed on Aug. 8, 2005, the contents of which are incorporated by reference herein.

BACKGROUND OF THE INVENTION

1. Field of the Invention

The present invention relates to an optical interrogation system which implements an over-clocking method that increases a read-out speed of a CCD (charge coupled device) detector (in this case part of a spectrometer) which enhances the ability to detect a minute/small biological event on or near a top surface of an optical biosensor.

2. Description of Related Art

Today optical sensor technology is being used in academia and industry to conduct studies associated with detecting a biological event on or near a top surface of an optical biosensor. In such studies, an optical interrogation system is used which has a launch system that couples light into an optical biosensor (e.g., resonant waveguide grating (RWG) biosensor). The light that is resonant with the optical biosensor is then out-coupled (reflected), and is captured by a receive system which analyzes the light to determine whether or not a biological event occurred on top of the RWG biosensor. In particular, the receive system analyzes the light to measure an optical response (resonant wavelength/angle) that indicates whether or not a biological event occurred on the top surface of the RWG biosensor. Unfortunately, such a receive system and in particular its CCD detector, which is used in industry today, may easily be saturated by the received light. Such, CCD detector saturation makes it difficult to detect minute shifts (e.g., sub-picometer wavelength shifts) in the optical response, which means it becomes difficult to detect small biological events on top of the RWG sensor (the reason this happens is discussed in detail below).

One way that was tried to address this saturation problem was to install an optical attenuator (e.g., variable optical attenuator (VOA)) within the launch system to reduce the intensity of the emitted light to a level which is below the saturation limit of the CCD array (e.g., pixels) within the spectrometer. However, the optical interrogation system has a signal-to-noise ratio (SNR) per unit of integration time which happens to be limited by the intensity of the light received at the CCD array in the spectrometer. Thus, the spectrometer's ability to locate the optical resonance is quantifiably related to the amount of power that the CCD array (pixels) is able to handle without saturating. As a result, if the spectrometer could be enhanced to handle a higher optical power level then it would be possible to detect small shifts in the optical response and hence detect small biological events on top of the RWG sensor. This need is satisfied by the present invention.

BRIEF DESCRIPTION OF THE INVENTION

An optical interrogation system is described herein that has a CCD array based spectrometer (e.g., detector array) which implements an over-clocking scheme that increases the spectrometer's read-out speed, allowing it to handle a higher optical power level so it can better detect a small biological event on top of an optical biosensor. In one embodiment, the optical interrogation system has a launch system which includes a light source that directs a light beam towards an optical biosensor. In addition, the optical interrogation system has a receive system which includes a spectrometer that has its CCD detector covered such that only a subset of pixels can receive a light beam out-coupled from the optical biosensor. The spectrometer further includes a controller (or control logic) which implements an over-clocking scheme that enables a set of charges associated with the received light beam to be transferred (simultaneously) out from the subset of pixels and into a shift register before the shift register outputs a previously transferred set of charges (note: the previously transferred set of charges had to be shifted "down stream" within the shift register before the new set of charges where simultaneously transferred from the subset of pixels into the shift register). The spectrometer also has a voltage converter that receives the previously transferred set of charges after they are output from the shift register and then converts them into a voltage signal. The receive system has an analog/digital converter that converts the voltage signal into a digital signal. Lastly, the receive system has a processor that processes the digital signal to determine the position of an optical response (resonant wavelength/angle) which indicates whether or not a biological event occurred on top of the optical biosensor.

BRIEF DESCRIPTION OF THE DRAWINGS

A more complete understanding of the present invention may be obtained by reference to the following detailed description when taken in conjunction with the accompanying drawings wherein.

DETAILED DESCRIPTION OF THE DRAWINGS

Figure 1:
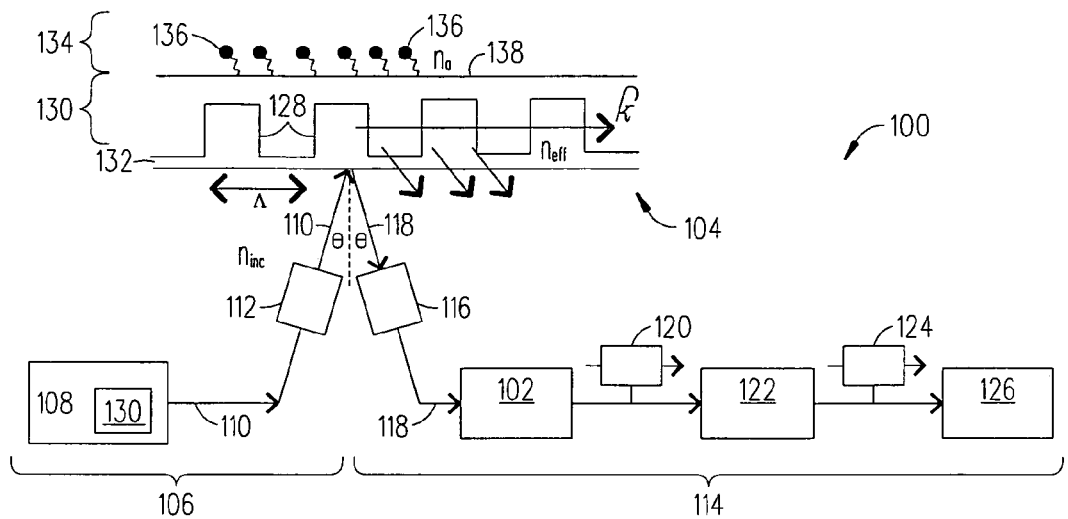
FIG. 1 is a block diagram of an optical interrogation system (incorporating an enhanced spectrometer) which is used to interrogate a RWG biosensor in accordance with the present invention.

Referring to FIG. 1, there is a block diagram of an exemplary optical interrogation system 100 (incorporating an enhanced spectrometer 102) which is used to interrogate a biosensor 104 (e.g., RWG biosensor 104) in accordance with the present invention. The optical interrogation system 100 includes a launch system 106 which has a light source 108 that outputs an optical beam 110 into a lensed fiber optic 112 which emits the optical beam 110 towards RWG biosensor 104. In addition, the optical interrogation system 100 includes a receive system 114 which has a lensed fiber optic 116 that receives an optical beam 118 reflected/out-coupled from the RWG biosensor 104. The receive system 114 also includes a spectrometer/detector array 102 (enhanced in accordance with the present invention) which receives the optical beam 118 emitted from the lensed fiber optic 116. The enhanced spectrometer 102 outputs a voltage signal 120 (representative of the resonant wavelength/angle of the RWG biosensor 104) to an analog-to-digital converter 122 (A/D converter 122). The A/D converter 118 converts the voltage signal 120 into a digital signal 124 which is received by a processor 126. The processor 126 uses a peak finding algorithm to process the digital signal 124 and locate an optical response (resonant wavelength) which indicates whether or not a biological event occurred on or near a top surface 138 of the RWG biosensor 104. How the spectrometer 102 is enhanced in accordance with the present invention is described in detail below after a brief description is provided about the optical interrogation system 100 and the RWG biosensor 104.

The RWG biosensor 104 (which is described in detail in U.S. Pat. No. 4,815,843) can best be explained by analyzing the structure of its diffraction grating 128 and waveguide 130. The optical beam 110 which is directed at the diffraction grating 128 can only be coupled into the waveguide 130 if its wave vector satisfies the following resonant condition shown in equation no. 1:

$$k'_x = k_x - \kappa \quad [1]$$

where $k_x'$ is the x-component of the incident wave vector, $k_x$ is the guided mode wave vector, and $\kappa$ is the grating vector. The grating vector $\kappa$ is defined as a vector having a direction perpendicular to the lines of the diffraction grating 128 and a magnitude given by $2\pi/\Lambda$ where $\Lambda$ is the grating period (pitch). This expression may also be written in terms of wavelength $\lambda$ and incident angle $\theta$ as shown in equation no. 2:

$$\frac{2\pi n_{inc}}{\lambda}\sin\theta = \frac{2\pi n_{eff}}{\lambda} - \frac{2\pi}{\Lambda} \quad [2]$$

where $\theta$ is the angle of incidence of the optical beam 110, $n_{inc}$ is the index of refraction of the incident medium, $\lambda$ is the wavelength of the optical beam 110, and $n_{eff}$ is the effective index of refraction of the waveguide 130. The waveguide 130 has an effective index of refraction which is a weighted average of the indices of refraction that the optical waveguide mode field "sees" as it propagates through the waveguide 130. The optical waveguide mode preferably has a spatial extent that is much wider than the waveguide 130, where the spatial extent depends on the refractive index of a substrate 132. As a result, the optical waveguide mode has an evanescent wave/tail that extends into the superstrate 134 (sensing region 134) which "sees" any surface changes created by a biological event such as when a biological substance 136 (e.g., cell, molecule, protein, drug, chemical compound, nucleic acid, peptide, carbohydrate) approaches or comes in contact with the biosensor's top surface 138.

Figure 2:
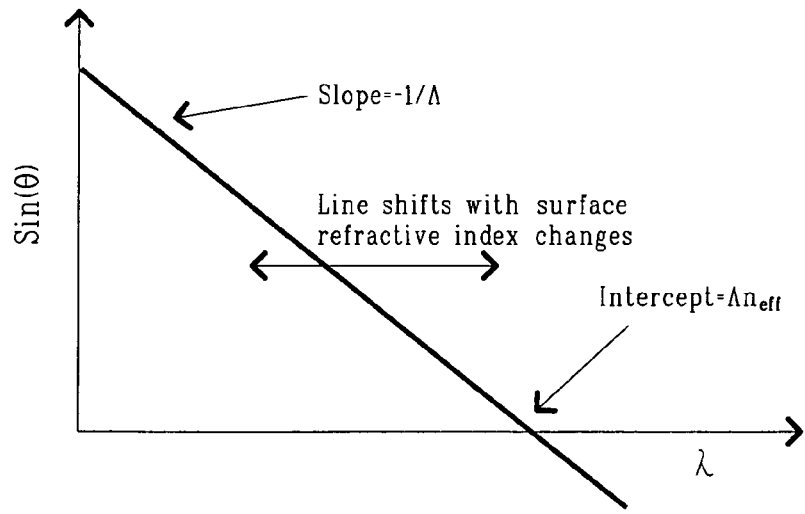
FIG. 2 is a graph that illustrates a relationship between a resonant angle and a resonant wavelength of the RWG biosensor shown in FIG. 1.

The expression shown in equation no. 2 may be rewritten in the more convenient form shown in equation no. 3:

$$\sin\theta = n_{eff} - \frac{\lambda}{\Lambda} \quad [3]$$

which is the equation of a line where $\sin\theta$ being the y axis, $\lambda$ being the x-axis, $\Lambda n_{eff}$ the x-intercept, and $-1/\Lambda$ the slope. To obtain equation no. 3, $n_{inc}$ is set to 1 so that it could be removed from this expression. This approximation is used since air (n~1.0003) is the most common incident medium. As such, when a biological substance 136 binds to the surface 138, then the effective index of the waveguide 130 is altered which leads to the shifting of the optical response (e.g., resonant wavelength or resonant angle) of the RWG biosensor 104. This shifting can be seen as a shift of the x-intercept in the line shown in FIG. 2.

Figure 3:
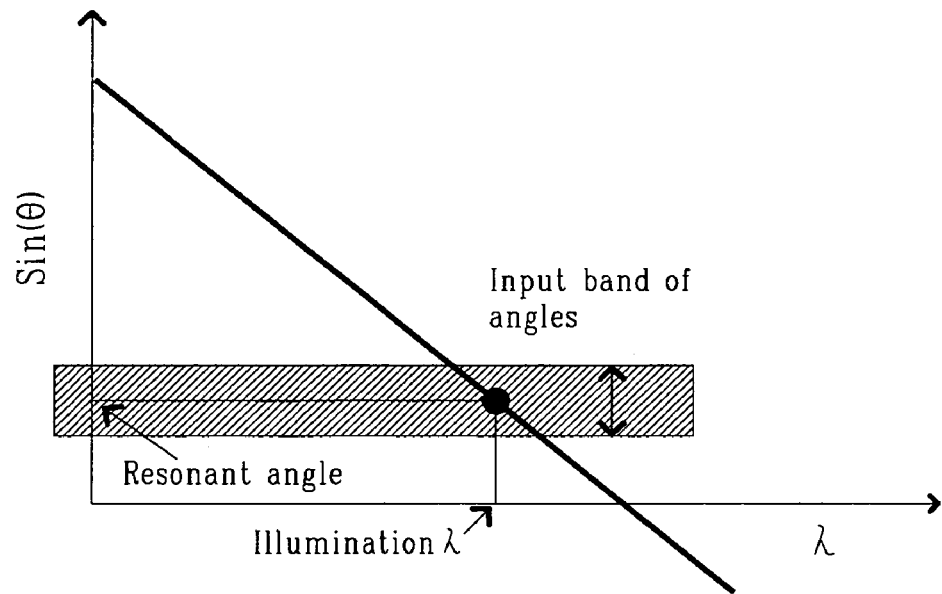
FIG. 3 is a graph used to help describe how a angular interrogation approach can be used by the optical interrogation system to determine the resonant angle of the RWG biosensor shown in FIG. 1.

The optical response (or resonant condition) of such a biosensor 104 may be observed by monitoring properties of the optical beam 118 that is reflected from the RWG biosensor 104. These properties, namely resonant wavelength or angle, change when the refractive index changes. Thus there are two different modes of operation for monitoring the refractive index changes of a RWG biosensor 104—angular interrogation or spectral interrogation—. In angular interrogation, a nominally single wavelength optical beam 110 is focused to create a range of illumination angles and then is directed into the RWG biosensor 104. The enhanced detector 102 (e.g., enhanced spectrometer 102) receives the reflected optical beam 118. And, by monitoring the position of the resonant angle reflected by the RWG biosensor 104, one can monitor the binding or refractive index changes on or near the biosensor's surface 138. The angular interrogation concept is graphically represented in the graph shown in FIG. 3.

Figure 4:
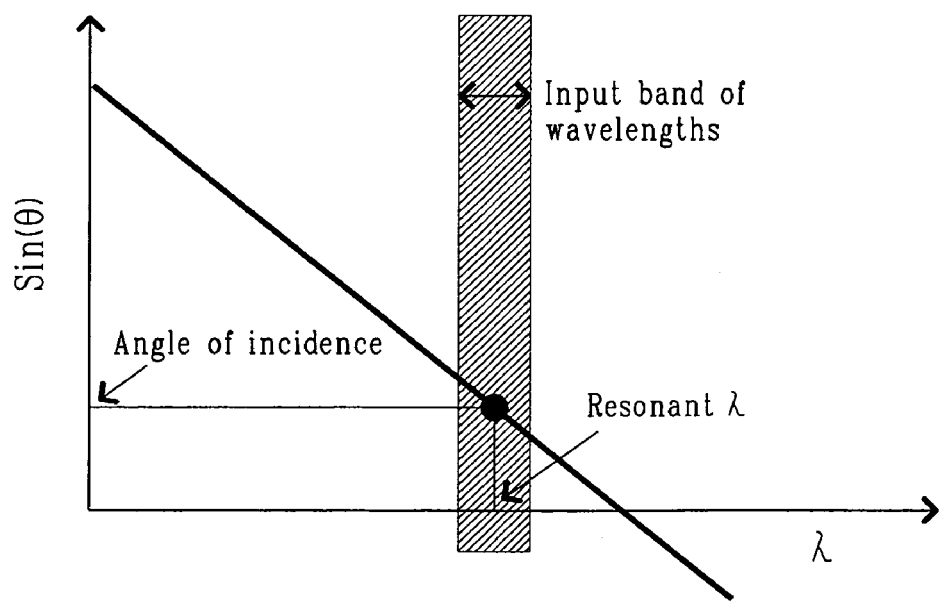
FIG. 4 is a graph used to help describe how an spectral interrogation approach can be used by the optical interrogation system to determine the resonant wavelength of the RWG biosensor shown in FIG. 1.

In spectral interrogation, a nominally collimated, broadband optical beam 110 is sent into the RWG biosensor 104 and the reflected optical beam 118 is collected and sent to the enhanced detector 102 (e.g., enhanced spectrometer 102). And, by observing the spectral location of the resonant wavelength (peak), one can monitor the binding or refractive index changes on or near the biosensor's surface 138. The spectral interrogation concept is graphically represented in the graph shown in FIG. 4.

Figure 5:
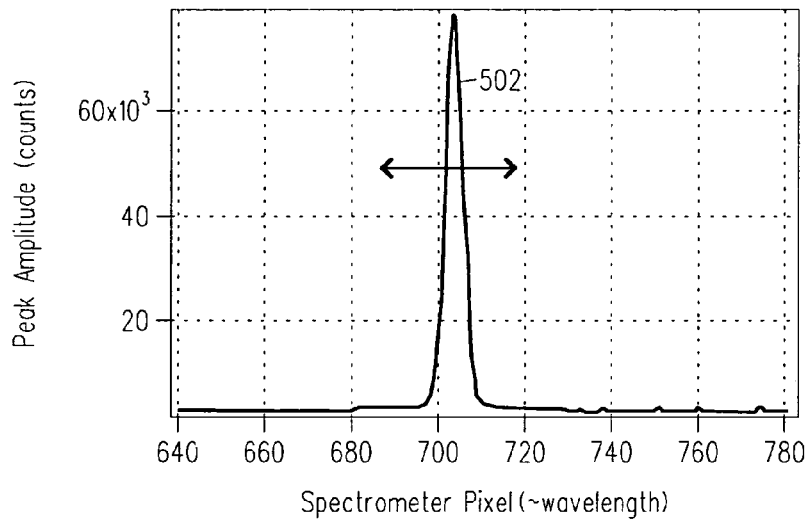
FIG. 5 is a graph illustrating an exemplary spectral signal that was observed by the optical interrogation system which used the spectral interrogation approach to interrogate the RWG biosensor shown in FIG. 1.

In the present invention, the focus is on the method of spectral interrogation (even though the present invention can also be used with the angular interrogation method which utilizes a similar array detector). In particular, the present invention details the technique of sending the reflected light beam 118 to an enhanced spectrometer 102 which uses a diffraction grating and a CCD array (e.g., pixels) to observe the reflected spectra (optical response) of RWG sensor 104. FIG. 5 is a graph which illustrates an exemplary spectral signal optical response observed by the optical interrogation system 100 which used a single mode/single mode dual fiber collimator 112 and 116. As the biological substance 136 binds to the RWG sensor 104, the refractive index changes which causes the resonant reflected peak 502 (optical response 502) in the spectrum to shift to a longer wavelength. The better that the optical interrogation system 100 is able to detect minute shifts in this resonant peak 502, then the better it can reliably detect a small biochemical binding event. The ability to detect a minute shift in the resonant peak 502 is a main advantage of implementing an over-clocking scheme within the spectrometer 102.

Figure 6:
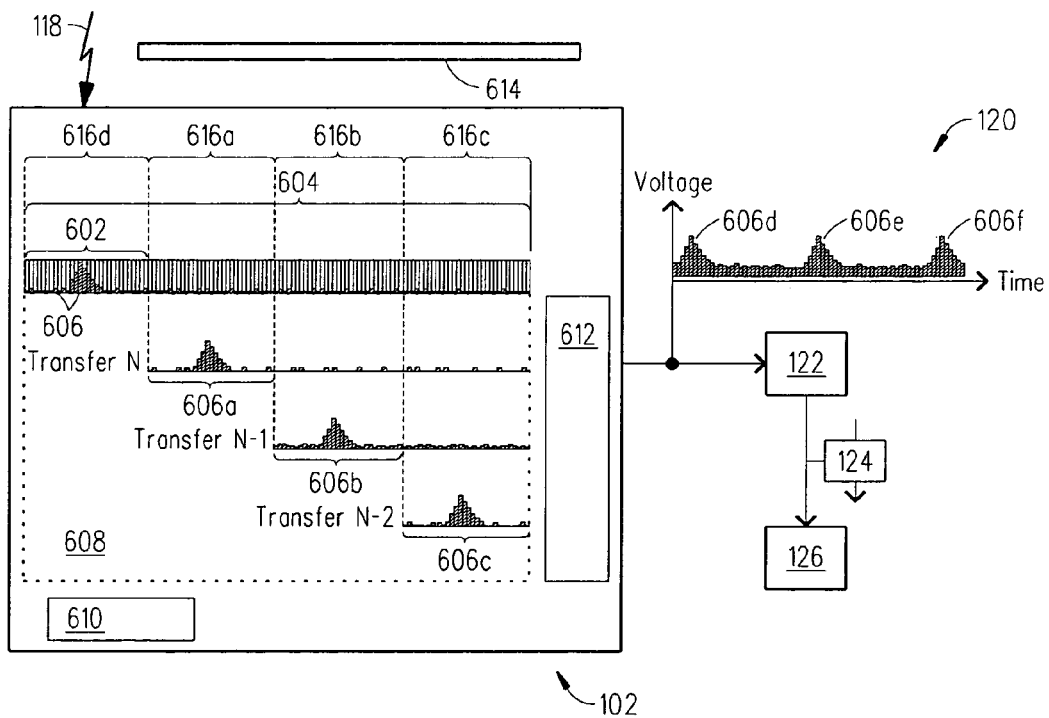
FIG. 6 is a block diagram illustrating the basic components of the spectrometer shown in FIG. 1 which has been enhanced in accordance with the present invention.

Referring to FIG. 6, there is a block diagram of a spectrometer 102 (e.g., detector array 102) which implements an over-clocking scheme that effectively enhances the ability to detect a small biological event (e.g., biological substance 136) on top of the RWG biosensor 104. The spectrometer 102 (e.g., 1D spectrometer 102) has a subset of pixels 602 (as compared to the total number of pixels 604) which responds to the optical power of the incident light beam 118 by producing a set of electrical charges 606 (electrons 606). The magnitudes of the electrical charges 606 relate directly to the intensity of the incident light beam 118. Plus, the electrical charges 606 constantly accumulate within the subset of pixels 602 (e.g., photon electron collection wells 602) until the end of an integration period at which point they are transferred into a shift register 608.

The spectrometer 102 has a processor 610 (or control logic 610) which controls when the set of electrical charges 606 is transferred into the shift register 608. In addition, the processor 610 (or control logic 610) controls when one or more set(s) of previously transferred charge(s) 606a, 606b and 606c are serially transferred out of the shift register 608 and into a voltage converter 612. The processor 610 implements an over-clocking scheme using these two capabilities where the set of electrical charges 606 is transferred into the shift register 608 before one or more set(s) of previously transferred charge(s) 606a, 606b and 606c are transferred out of the shift register 608. In other words, multiple sets of transferred charges 606, 606a and 606b can be transferred out of the subset of pixels 602 and into the shift register 608 before one set of previously transferred charges 606c is shifted out of the shift register 608.

In the illustrated example, the processor 610 transfers the set of electrical charges 606 into the shift register 608 and at the same the set of electrical charges 606c (which was transferred into the shift register 608 at integration period N−2) is transferred out of the shift register 608 and into the voltage converter 612. Also, when the set of electrical charges 606 is transferred into the shift register 608, those electrical charges 606 are added in a serial fashion to the two sets of electrical charges 606a and 606b still present within the shift register 608. As shown, the two sets of electrical charges 606a and 606b were respectively transferred into the shift register 608 during integration periods N and N−1. The over-clocking scheme is a marked improvement over a traditional clocking scheme in which all of the electrical charges located within the shift register 608 needed to be shifted out of the shift register 608 before one was able to transfer a new set of electrical charges into the shift register 608.

As can be seen, the over-clocking scheme increases a rate at which electrical charges 606, 606a, 606b and 606c can be transferred out of the subset of pixels 602 and into the shift register 608. Again, an optical power level is typically limited so that individual exposed CCD pixels do not saturate before their charge can be transferred out. However, by increasing the rate at which charge can be transferred out of the exposed CCD pixels 602, the optical power handling capability of the spectrometer 102 can be increased which makes it possible to detect a small/minute biological event on top of the RWG sensor 104. As shown, the over-clocking scheme is preferably implemented when a sub-region of the total number of pixels 604 within the spectrometer 102 is illuminated with incident light 118 that is reflected from the RWG biosensor 104. To accomplish this, an optical shutter 614 can be used to block a portion of the spectrometer 102. In one embodiment, the optical shutter 614 is a piece of metal which is made to translate (via a screw adjustment) in front of the pixels 604 to block/shade most of the pixels 604 (see over-clocking regions 616a, 616b and 616c). The optical shutter 614 effectively controls how many of the pixels 604 are to be shaded/un-shaded so the amount of "over-clocking" can be adjusted. In this example, the optical shutter 614 is positioned where only the subset of pixels 602 (associated with over-clocking region 616d) is able to receive the incident light beam 118 that is reflected from the RWG sensor 104.

Once, the set of electrical charges 606a, 606b and 606c are transferred into the shift register 608 then they are serially shifted towards one end of the shift register 608 where individual charges within a specific set of charges 606c (for example) will eventually be transferred into the voltage converter 612. The voltage converter 612 converts the individual electrical charges 606c into an analog signal 120. If desired, the voltage converter 612 can amplify the analog signal 120. In the illustrated example, the analog signal 120 contains voltages associated with three previous sets of electrical charges 606d, 606e and 606f. The A/D converter 122 (shown as being external to the spectrometer 102) receives the analog signal 120 and converts the analog signal 120 into a digital signal 124. The processor 126 (e.g., personal computer 126, digital signal processor 126, field-programmable gate array (FPGA) 126) receives the digital signal 124 and uses a peak finding algorithm to process the digital signal 124 to locate the optical response which indicates whether or not a biological event occurred on top of the RWG biosensor 104.

In one embodiment, the processor 126 can crop the digital signal 124 into individual signals based on the size of the over-clocking region 616d (which corresponds to the size of the subset of pixels 602). Then, the processor 126 can use a peak finding algorithm to process an individual digital signal (waveform) to locate the optical response which indicates whether or not a biological event occurred on top of the RWG biosensor 104. Alternatively, the processor 126 can accumulate the various signals (waveforms) associated with previously transferred sets of charges 606d, 606e and 606f into a single waveform. Then, the processor 126 can use a peak finding algorithm to process the single accumulated waveform to monitor the movement of the optical response over time which indicates when a biological event occurred on top of the RWG biosensor 104.

The over-clocking scheme could be applied to different types of array detector architectures including, for example, a CCD array and a CMOS (complementary metal oxide semiconductor) array. In fact, an array detector which does not use a charge shift register 608 but instead uses pixels which have their own charge-to-voltage converters could be used in the present invention. The over-clocking scheme can still be used with this type array detector, because the electrical charge is able to be removed from an integration device/charge accumulation device which is located at each pixel faster than the voltage from each charge-to-voltage converter can be clocked-out. Fundamentally, removing a charge from a sub-region of the charge accumulation device faster than the entire array of "charges" can be read-out of the detector array is a main feature of the over-clocking scheme. In this way, the power handling capability of the detector 102 can be increased by a factor of N, where N is the ratio of the number of pixels in the entire array 604 to the number of pixels 602 in the over-clocking region 606. However, the spectral dynamic range of the detector 102 happens to be reduced, because only a small spectral window is illuminated and captured when using the over-clocking scheme.

There are at least three ways that the over-clocking scheme can help improve/benefit the optical interrogation system 100:

1. Higher optical power saturation limit: Using the over-clocking scheme, one can extend the optical power saturation limit of the spectrometer 102 (detector array 102)

by transferring more charges out of the device per unit time. This results in higher SNR measurements.

2. Higher "frames per second": An additional benefit of using the over-clocking scheme is that the signal of interest (within the over-clocking region 616d) is clocked out at a faster rate. This can be advantageous when the optical interrogation system 100 is used to look at time based transients within measurement applications. In addition, it can be advantageous when the optical interrogation system 100 is used in control application with a real time feedback measurement.

3. Lower pixel clock rate for same optical power saturation limit and frame rate: If a system's noise source is predominately read-out noise, then the over-clocking scheme can be deployed to reduce the overall pixel clock rate, while still maintaining the same optical power saturation limit. By reducing the pixel clock rate, it is possible to more effectively filter the analog waveform before it reaches the A/D converter 122 which helps to average down the electrical noise from the spectrometer 102 (detector array 102).

Note: these primary benefits can be mixed together in the same solution. For instance, it is possible to have a higher saturation limit, and reduce the clock rate if that is desired. The limit to how much can be done is governed by the number of over-clocking regions 616a, 616b, 616c, and 616d located within the spectrometer 102 (detector array 102). For example, a spectrometer 102 which has a 1D array of 2000 pixels with 50 pixels per each over-clocking region would have 40 over-clocking regions. This can be used to increase the saturation limit of the spectrometer 102 (detector array 102) by 10× and reduce the clocking rate by 4×. Of course, the specific application may govern how to trade-off the two potential benefits.

As described above, the over-clocking scheme effectively increases the optical power saturation limit of the spectrometer 102 which also increases the SNR achieved per unit time, making it possible to detect a minute change in the position of the optical response of the RWG biosensor 104. A discussion is provided next about why an over-clocking scheme helps increase the SNR when a RWG biosensor 104 is interrogated by an optical interrogation system 100 (e.g., label-independent optical interrogation system 100).

In general, the ability of the optical interrogation system 100 to resolve the location of a resonance peak (optical response) is a function of SNR. The theoretical resolution limit of locating the resonance peak is indicated in the following equation:

$$\delta\lambda_{res} \approx \frac{\Delta\lambda_{peak}}{SNR}. \quad [4]$$

The above expression is approximate, and to be completely accurate it needs to multiplied by a factor close to 1 where the exact value of the factor depends on the functional form of the peak shape (Gaussian, Lorenztian, etc.).

For a broadband spectral detection receive system 114, the SNR (based on source power) that a CCD system 102 can achieve on a resonance peak is given by:

$$\left(\frac{\# \text{ photo } e^-}{\sec}\right) = \left(\frac{SNR^2}{T_{int}}\right) = \frac{QE \cdot \varepsilon \cdot P_s(\lambda) \cdot \Delta\lambda_{peak}}{\left(\frac{hc}{\lambda}\right)} \quad [5]$$

where $$SNR = \sqrt{\frac{QE \cdot \varepsilon \cdot P_s(\lambda) \cdot \Delta\lambda_{peak}}{\left(\frac{hc}{\lambda}\right)}} \sqrt{T_{int}}$$

(SNR based on available source power)

Here QE is the quantum efficiency of the detector, $\varepsilon$ is the optical efficiency of the overall system, $P_s(\lambda)$ is the power spectral density of the optical source (W/nm), $\Delta\lambda_{peak}$ is the spectral width of the resonance peak, and $T_{int}$ is the integration time utilized by the optical interrogation system 100. Also, h is defined as Planck's constant, c is the speed of light, and $\lambda$ is the wavelength of the resonance such that (hc/$\lambda$) is the energy of a photon in Joules. In this analysis, a shot-noise limited performance is assumed, so that the SNR is the square root of the number of photo electrons observed within a resonance peak. As a result, equations 4 and 5 can be combined to obtain the following:

$$\delta\lambda_{res} \cdot \sqrt{T_{int}} \approx \frac{\sqrt{\Delta\lambda_{peak}}}{\sqrt{QE \cdot \varepsilon \cdot P_s(\lambda)}} \sqrt{\frac{hc}{\lambda}} \quad [6]$$

(F.O.M.–power limited by source)

This expression is a figure-of-merit (F.O.M.) for the optical interrogation system 100, with the units being fm/(Hz)$^{1/2}$. The lower this value is, then the better the detection system 114 is able to resolve a resonant peak in a given amount of time. As can be seen, it is beneficial to have a narrower resonance, a higher quantum efficiency (or optical efficiency), and a greater source power spectral density. However, as long as the optical source 106 has enough power to saturate the spectrometer 102 (detector array 102), then the optical interrogation system 100 is not limited by the photons available from the light source 108, but instead it is limited by the power handling capability of the spectrometer 102 (detector array 102). As a result, the F.O.M. for the optical interrogation system 100 should be expressed in terms of the speed parameters of the CCD array 102.

To determine this F.O.M., we make use of the fact that the maximum rate of photo electrons per sec, R, which a given CCD pixel can handle is given by the well depth (or saturation level) of a pixel (in electrons), $N_{sat}$, times the video read rate (or frame rate) of the of the entire CCD array, $R_{video}$. This relationship is expressed as follows:

$$R = N_{sat} \cdot R_{video}. \quad [7]$$

And, when the peak starts to saturate the CCD array 102, then this rate R may be expressed as follows:

$$R \approx 2 \cdot \left(\frac{\text{Total photo } e^- \text{ in peak}}{\sec}\right) = 2 \cdot \frac{\left(\frac{SNR^2}{T_{int}}\right)}{(\Delta\lambda_{peak}/\Delta\lambda_{pixel})} \quad [8]$$

where $\Delta\lambda_{pixel}$ is the spectral width of a CCD pixel (in pm) Next, equations 7 and 8 can be combined to obtain the following:

$$SNR = \sqrt{\frac{1}{2} \cdot \frac{N_{sat} \cdot R_{video} \cdot \Delta\lambda_{peak}}{\Delta\lambda_{pixel}}} \quad [9]$$

$\sqrt{T_{int}} \cdot (SNR$ based on $CCD$ saturation)

Now, this SNR expression is placed into the theoretical resolution limit formula (equation 4) to obtain the following:

$$\delta\lambda_{res} \cdot \sqrt{T_{int}} = \sqrt{2} \sqrt{\Delta\lambda_{peak}} \sqrt{\Delta\lambda_{pixel}} \sqrt{\frac{1}{N_{sat} \cdot R_{video}}} \quad [10]$$

(F.O.M.-power limited by detector saturation)

This equation is a F.O.M (fm/(Hz)$^{1/2}$) which has parameters that are associated with the spectrometer 102 (detector array 102). Again, a narrow resonance is beneficial for performance. However, now it can be seen that the more photons a CCD array 102 can handle as expressed by the product of the well depth and the video read rate then the better the F.O.M. Narrow pixels also help in that, for a fixed well depth, a spectrometer 102 (detector array 102) with more pixels can handle more photons in a given resonance peak.

A challenge with many CCD based spectrometers 102 is that they are designed to handle low light levels, and normally have only modest optical power handling capability before saturating. To boost the power handling capability of the spectrometer 102, the over-clocking scheme is used to effectively increase the video read rate $R_{video}$. Basically, the over-clocking scheme and the optical shutter 614 turn the CCD array 102 into a concatenation of shorter CCD arrays (see over-clocking regions 616a, 616b ... 616d) each of which has a much faster video read rate $R_{video}$ than that of a larger CCD array (see pixels 604). If the clock rate of shuffling data out of an individual pixel is $R_{clock}$, then:

$$R_{video} = N_{pix} \cdot R_{clock}. \quad [11]$$

As can be seen, one can effectively increase the video read rate by shortening the useful portion of the CCD array (so fewer pixels are utilized), even if the clock rate of the individual pixels is held constant. Thus, the power handing capability of the spectrometer 102 is improved which in turn improves the overall peak resolution in a given integration time (F.O.M.). This enables one to detect a small biological event on top of an RWG biosensor 104.

From the forgoing, it should be appreciated that one's ability to determine the position of the resonance peak is dependent on the SNR of the measurement, where the higher the SNR, the better one can resolve the wavelength position of the optical signal. Since, there is normally a surplus of optical power for a spectrometer 102 (detector array 102), the over-clocking scheme effectively enhances this type of measurement by increasing the optical power saturation limit of the spectrometer 102 by at least 10×, and hence the SNR is increased by 3.3×. Of course, the optical interrogation system 100 shown in FIG. 1 is just one type of system that is improved by incorporating an enhanced spectrometer 102. Several other types of optical interrogation systems which could be improved by incorporating an enhanced spectrometer 102 are disclosed in the following co-assigned patent applications:

U.S. patent application Ser. No. 11/027,547 entitled "Spatially Scanned Optical Reader System and Method for Using Same".

U.S. patent application Ser. No. 10/977,520 entitled "Single-Fiber Launch/Receive System for Biosensing Applications".

U.S. patent application Ser. No. 10/856,572 entitled "Optical Interrogation Systems With Reduced Parasitic Reflections and a Method for Filtering Parasitic Reflections".

U.S. patent application Ser. No. 11/058,155 entitled "Single Mode (SM) Fiber Optical Reader System and Method for Interrogating Resonant Waveguide-Grating Sensor(s)".

U.S. Patent Application Ser. No. 60/701,445 entitled "Label-Free High Throughput Biomolecular Screening System and Method".

U.S. patent application Ser. No. 10/602,304 entitled "Optical Interrogation System and Method for Using Same".

U.S. patent application Ser. No. 11/019,439 entitled "Arrayed Sensor Measurement System and Method"

U.S. Pat. No. 6,785,433 entitled "Waveguide Grid Array and Optical Measurement Arrangement".

U.S. patent application Ser. No. 11/100,199 entitled "Optical Interrogation System and Method for 2-D Sensor Arrays".

The contents of these documents are incorporated by reference herein.

Figure 7:
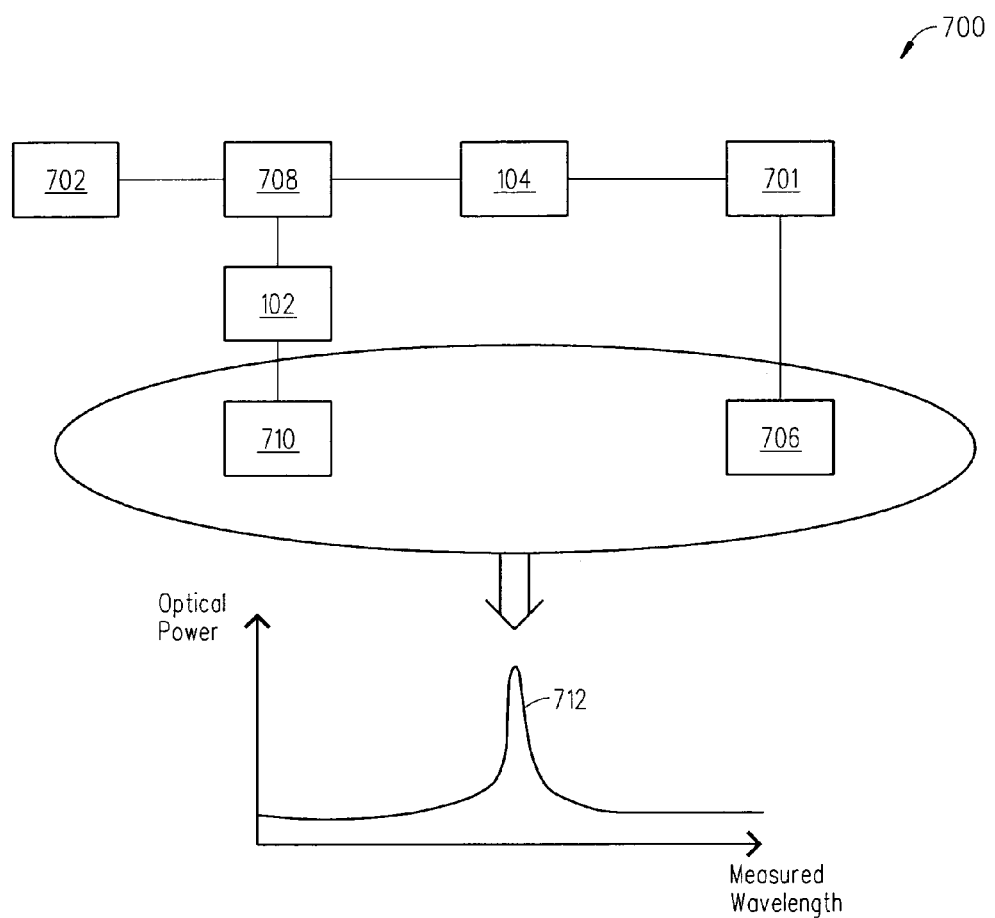
FIG. 7 is a block diagram of an optical interrogation system that has a different configuration than the one shown in FIG. 1 but still can be used to interrogate a RWG biosensor in accordance with the present invention.

Referring to FIG. 7, there is shown an optical interrogation system 700 which can utilize one photodetector (e.g. photodiode) 701 and one enhanced spectrometer 102 in accordance with another embodiment of the present invention. As shown, a tunable laser 702 (light source 702) interrogates a RWG sensor 104 (or LID sensor 104) such that the out-coupled light is detected by a power sensitive photodetector 701 (or other single element photodiode/CCD device 701). The photodetector 701 outputs an optical spectrum 706 representative of reflected power 706 which is a function of time. In this embodiment, the determination of the exact wavelength of the tunable laser 702 at any given instant during the sweep is important so one can accurately reconstruct the spectra 706. To accomplish this, the tunable laser 702 is swept over a particular wavelength range. And, a portion of the power from the tunable laser 702 is split off by a 1×2 splitter 708 and directed into the wavelength reference spectrometer 102. The rest of the power from the 1×2 splitter 708 is sent through the RWG sensor 104 and onto the power detector 701. The reference wavelength 710 (obtained from spectrometer 102) and the optical power spectrum 706 (obtained from the power detector 701) are synchronously acquired so as to form the waveform 712. The resulting waveform 712 exhibits the optical power 706 as the Y-axis, and the reference wavelength 710 as the X-axis. It is possible to perform this measurement without the reference spectrometer 102, however, its presence and use relaxes the stability requirements of the tunable laser 702. For instance, as the tunable laser 702 is stepped, it may not settle and operate to the exact wavelength it was commanded to reach. This would distort the X-axis in the resulting waveform 712. Thus, by measuring the actual wavelength with the reference spectrometer 102 at each step, it is possible to compensate for any wavelength instability of the tunable laser 702.

Following are some additional advantages, features and uses of the present invention:

The over-clocking technique increases the read-out speed of a linear or two-dimensional spectrometer 102 when a fraction of the pixels filled by the optical signal 118 is small.

The over-clocking technique increases the read-out speed of the spectrometer 102 by one order of magnitude.

The over-clocking technique increases the optical power saturation level of the spectrometer 102 by at least one order of magnitude.

The over-clocking technique increases the SNR of the detected signal 118 by at least 3.3×.

The over-clocking technique achieves high read-out rates while preserving the spatial/spectral dynamic range of a large spectrometer.

The over-clocking technique could be applied to detectors used in spectrographs because these devices can be used to receive a spatially/spectrally narrow optical signal.

Although two embodiments of the present invention have been illustrated in the accompanying Drawings and described in the foregoing Detailed Description, it should be understood that the invention is not limited to the disclosed embodiments, but is capable of numerous rearrangements, modifications and substitutions without departing from the spirit of the invention as set forth and defined by the following claims.

What is claimed is:

1. A method for increasing a read-out speed of a 1-D detector within an optical interrogation system, the optical interrogation system includes a launch system and a receive system, wherein said launch system directs a light beam towards a biosensor, and wherein said receive system includes a 1-D detector which receives a light beam out-coupled from said biosensor, the method comprising the steps of:
   blocking a plurality of pixels located within said 1-D detector such that only a subset of pixels receive the light beam out-coupled from said biosensor;
   transferring a set of charges/voltages associated with the received light beam from the subset of pixels located within said 1-D detector before outputting from said 1-D detector a signal representative of a previously transferred set of charges/voltages associated with a previously received light beam; and
   processing the signal in a first-in and first-out sequence to determine an optical response corresponding to the previously transferred set of charges/voltages, wherein said optical response indicates whether or not there was a biological substance/bio-chemical interaction on top of said biosensor.

2. An optical interrogation system, comprising:
   a launch system including:
      a light source that directs a light beam towards a biosensor; and
   a receive system including:
      an optical shutter
      a detector comprising:
         a subset of pixels that receives an out-coupled light beam from said biosensor, wherein the optical shutter blocks a plurality of pixels located within said detector such that only the subset of pixels receive the light beam out-coupled from said biosensor;
         a controller that causes a set of charges/voltages associated with the received light beam to be transferred out from said subset of pixels before a voltage signal representative of a previously transferred set of charges/voltages associated with a previously received light beam is outputted from said detector; and
      an analog/digital converter that converts the voltage signal into a digital signal representative of the previously transferred set of charges/voltages; and
      a processor that processes the digital signal in a first-in and first-out sequence to determine an optical response corresponding to the previously transferred set of charges/voltages, wherein said optical response indicates whether or not there was a biological substance/bio-chemical interaction on top of said biosensor.

3. The optical interrogation system of claim 2, wherein said 1-D detector is:
   a 1-D spectrometer;
   a 1-D CCD detector; or
   a 1-D CMOS detector.

4. The optical interrogation system of claim 2, wherein said receive system further includes a reference detector that receives a portion of the light beam directed towards the biosensor.

5. The optical interrogation system of claim 2, wherein said biosensor is a resonant waveguide grating biosensor.

6. The optical interrogation system of claim 2, wherein said biosensor is incorporated within a well of a microplate.

7. A method for increasing a read-out speed of a 1-D detector within an optical interrogation system, the optical interrogation system includes a launch system and a receive system, wherein said launch system directs a light beam towards a biosensor, and wherein said receive system includes a 1-D detector which receives a light beam out-coupled from said biosensor, the method comprising the steps of:
   blocking a plurality of pixels located within said 1-D detector such that only a subset of pixels receive the light beam out-coupled from said biosensor;
   transferring a set of charges/voltages associated with the received light beam from the subset of pixels located within said 1-D detector before outputting from said 1-D detector a signal representative of a previously transferred set of charges/voltages associated with a previously received light beam;
   processing the signal in a first-in and first-out sequence to determine an optical response corresponding to the previously transferred set of charges/voltages, wherein said optical response indicates whether or not there was a biological substance/bio-chemical interaction on top of said biosensor;
   wherein the combination of the blocking and transferring steps improve the processing step by:
      extending an optical power saturation limit of the 1-D detector by transferring more charges out per unit time than is possible without the blocking and transferring steps, where the extended optical power saturation limit results in higher signal-to-noise ratio, SNR, measurements which makes it easier to detect a change in a position of the optical response of the biosensor.

8. A method for increasing a read-out speed of a 1-D detector within an optical interrogation system, the optical interrogation system includes a launch system and a receive system, wherein said launch system directs a light beam towards a biosensor, and wherein said receive system includes a 1-D detector which receives a light beam out-coupled from said biosensor, the method comprising the steps of:

blocking a plurality of pixels located within said 1-D detector such that only a subset of pixels receive the light beam out-coupled from said biosensor;

transferring a set of charges/voltages associated with the received light beam from the subset of pixels located within said 1-D detector before outputting from said 1-D detector a signal representative of a previously transferred set of charges/voltages associated with a previously received light beam;

processing the signal in a first-in and first-out sequence to determine an optical response corresponding to the previously transferred set of charges/voltages, wherein said optical response indicates whether or not there was a biological substance/bio-chemical interaction on top of said biosensor;

wherein the combination of the blocking and transferring steps improve the processing step by:

extending an optical power saturation limit of the 1-D detector by transferring more charges out per unit time than is possible without the blocking and transferring steps, where the extended optical power saturation limit results in higher signal-to-noise ratio, SNR, measurements which makes it easier to detect a change in a position of the optical response of the biosensor; and reducing an overall pixel clock rate in the 1-D detector more than is possible without the blocking and transferring steps, where the reduced pixel clock rate averages down electrical noise from the 1-D detector; and limiting the extending step and the reducing step based on a specific application to trade-off benefits of extending the optical power saturation limit of the 1-D detector and reducing the overall pixel clock rate in the 1-D detector.

9. The method of claim 8, wherein said processing step further includes cropping the signal into individual signals and using a peak finding algorithm to process each individual signal to locate the optical response.

10. The method of claim 8, wherein said processing step further includes accumulating multiple signals associated with previously transferred sets of charges/voltages and using a peak finding algorithm on the accumulated signals to monitor a movement of the optical response over time which indicates when the biological substance/bio-chemical interaction occurred on the top of said biosensor.

* * * * *